US010945664B1

(12) United States Patent
Webb

(10) Patent No.: US 10,945,664 B1
(45) Date of Patent: Mar. 16, 2021

(54) PROTECTIVE CASE WITH COUPLING GASKET FOR A WEARABLE ELECTRONIC DEVICE

(71) Applicant: Apple Inc., Cupertino, CA (US)

(72) Inventor: Michael J. Webb, Scotts Valley, CA (US)

(73) Assignee: Apple, Inc., Cupertino, CA (US)

( * ) Notice: Subject to any disclaimer, the term of this patent is extended or adjusted under 35 U.S.C. 154(b) by 226 days.

(21) Appl. No.: 15/253,846

(22) Filed: Aug. 31, 2016

Related U.S. Application Data

(60) Provisional application No. 62/235,366, filed on Sep. 30, 2015.

(51) Int. Cl.
| | |
|---|---|
| *A61B 5/00* | (2006.01) |
| *A61B 5/0205* | (2006.01) |
| *A61B 5/1455* | (2006.01) |
| *A45C 11/00* | (2006.01) |

(52) U.S. Cl.
CPC .............. *A61B 5/681* (2013.01); *A45C 11/00* (2013.01); *A61B 5/0059* (2013.01); *A61B 5/6824* (2013.01)

(58) Field of Classification Search
CPC .... A44C 5/00; A44C 5/14; A44C 5/20; A45C 11/00; A45C 13/008; A45C 2011/001; A45C 2011/002; A45C 2200/10; G04B 37/10; G04B 37/005; H04B 2001/3894; G04G 17/08; A45F 2200/0508; A45F 5/00; A45F 2005/008; A45F 2200/0516
USPC ........................................................ 600/476
See application file for complete search history.

(56) References Cited

U.S. PATENT DOCUMENTS

| | | | |
|---|---|---|---|
| 4,657,320 A | 4/1987 | Bamford et al. |
| 5,111,363 A | 5/1992 | Yagi et al. |
| 5,125,846 A | 6/1992 | Sampson et al. |
| 6,344,877 B1 | 2/2002 | Gowda et al. |
| 6,866,544 B1 | 3/2005 | Casey et al. |
| 7,106,261 B2 | 9/2006 | Nagel et al. |
| 7,123,292 B1 | 10/2006 | Seeger et al. |
| 7,130,174 B2 | 10/2006 | Mayai et al. |
| 7,380,948 B2 | 6/2008 | Schofield et al. |
| 7,619,899 B2 | 11/2009 | Rubenstein et al. |
| 7,822,338 B2 | 10/2010 | Wernersson |

(Continued)

FOREIGN PATENT DOCUMENTS

WO  WO2012058295  5/2012

OTHER PUBLICATIONS

Author Unknown, "Copper Flex Products," www.molex.com, 6 pages, at least as early as Jul. 22, 2014.

*Primary Examiner* — Jon Eric C Morales
(74) *Attorney, Agent, or Firm* — Morgan, Lewis & Bockius LLP

(57) ABSTRACT

A protective case for a wearable electronic device. The wearable electronic device may include a housing and a band that is configured to secure the wearable electronic device to a user. A protective of removable case may be configured to attach to the external features of the housing and include a body portion and a set of curved protrusions that extend from the body portion to cover the corners of the housing. The device may include an optical sensor and the case may include an aperture formed in the body portion that is substantially aligned with the optical sensor. A gasket, positioned along a perimeter of the aperture, may be configured to provide an optical barrier for the optical sensor of the device.

12 Claims, 11 Drawing Sheets

(56) References Cited

U.S. PATENT DOCUMENTS

| | | |
|---|---|---|
| 7,978,489 B1 | 7/2011 | Telefus et al. |
| 7,989,709 B2 | 8/2011 | Tsao |
| 8,361,830 B2 | 1/2013 | Yang et al. |
| 8,385,258 B2 | 2/2013 | Perlman |
| 8,430,402 B2 | 4/2013 | Diehl et al. |
| 8,500,456 B1 | 8/2013 | Holec et al. |
| 8,708,746 B2 | 4/2014 | Altice et al. |
| 8,730,372 B2 | 5/2014 | Dabov |
| 8,905,684 B2 | 12/2014 | Waggle et al. |
| 9,035,326 B2 | 5/2015 | Cho |
| 9,074,915 B2 | 7/2015 | Kalhoff et al. |
| 9,209,627 B2 | 12/2015 | Baarman et al. |
| 2005/0095410 A1 | 5/2005 | Mazurkiewicz |
| 2005/0233122 A1 | 10/2005 | Nishimura et al. |
| 2007/0032130 A1 | 2/2007 | Yoshino |
| 2009/0213232 A1 | 8/2009 | Asakura et al. |
| 2010/0141571 A1 | 6/2010 | Chiang et al. |
| 2010/0177080 A1 | 7/2010 | Essinger et al. |
| 2011/0133208 A1 | 6/2011 | Nakahara |
| 2011/0155417 A1 | 6/2011 | Hu et al. |
| 2011/0304763 A1 | 12/2011 | Choi et al. |
| 2012/0081852 A1* | 4/2012 | Maravilla .............. A45F 5/00 361/679.03 |
| 2012/0270420 A1 | 10/2012 | Lapidot |
| 2013/0082984 A1 | 4/2013 | Drzaic et al. |
| 2014/0111953 A1 | 4/2014 | McClure et al. |
| 2014/0268522 A1* | 9/2014 | Tanaka ................ A61B 5/681 361/679.01 |
| 2014/0342577 A1 | 11/2014 | De Bruijn |
| 2015/0116958 A1 | 4/2015 | Shedletsky et al. |
| 2015/0138700 A1 | 5/2015 | Goyal et al. |
| 2015/0146355 A1 | 5/2015 | Goyal et al. |
| 2015/0194753 A1 | 7/2015 | Raff et al. |
| 2015/0295332 A1 | 10/2015 | Shedletsky et al. |
| 2016/0021742 A1 | 1/2016 | Johansson et al. |
| 2016/0028173 A1 | 1/2016 | Bosscher et al. |
| 2016/0029503 A1 | 1/2016 | Shedletsky et al. |
| 2016/0317086 A1* | 11/2016 | Smith .................. A61B 5/681 |
| 2017/0035156 A1* | 2/2017 | Wright ................ A45C 13/008 |

\* cited by examiner

PROTECTIVE CASE WITH COUPLING GASKET FOR A WEARABLE ELECTRONIC DEVICE

CROSS-REFERENCE TO RELATED APPLICATION(S)

This application is a non-provisional patent application of and claims the benefit of U.S. Provisional Patent Application No. 62/235,366, filed Sep. 30, 2015 and titled "Case with Coupling Gasket," the disclosure of which is hereby incorporated herein by reference in its entirety.

FIELD

Embodiments described herein relate generally to a wearable electronic device, and more particularly to a protective case for a wearable electronic device.

BACKGROUND

Portable electronic devices have become ubiquitous in recent years. Because of their ability to provide everyday personal and business functions to users, users have become accustomed to carrying these devices with them at all times. Because users are in possession of these devices in a variety of environments and for a variety of different activities, the devices may be susceptible to an impact or shock events. Therefore, there is a need for protective accessories that reduce the likelihood of damage due to shock or impact. It may also be desirable that the device perform otherwise as intended when a protective accessory is installed. The embodiments described herein are directed to protective accessories and, in particular, a protective case for a wearable electronic device.

SUMMARY

Embodiments providing a protective case for a wearable electronic device are described herein. Various embodiments described herein include a body portion configured to at least partially cover a housing of the wearable electronic device. The body portion may comprise one or more curved corner protrusions that are configured to cover one or more corners of the housing. An aperture may be formed in the body portion and a gasket may be formed around the aperture to form a protrusion in the body portion.

Some example embodiments are directed to a protective case for a wearable electronic device. The protective case includes a body portion configured to at least partially cover a housing of the wearable electronic device and includes a set of curved corner protrusions, each configured to cover a respective corner of a set of corners of the housing. The protective case may also include a gasket having a protrusion extending from a surface of the body portion and formed around an aperture defined in the body portion. The protrusion may be configured to contact a skin of a wearer when the wearable electronic device is attached to the wearer. In some cases, the gasket is integrally formed with the body portion.

In some embodiments, the wearable electronic device includes an optical sensor used to compute a health metric of the wearer. The optical sensor may be positioned adjacent to the aperture defined in the body portion of the protective case. The contact between the protrusion of the gasket and the wearer's skin shields the optical sensor from external light. In some cases, the gasket is formed from a compliant material that is configured to conform to a wrist of the wearer to form an optical seal.

In some embodiments, each corner of the set of corners of the housing has a contoured shape. Each curved corner protrusion of the set of curved corner protrusions may be formed from a compliant material and configured to conform to the contoured shape of the set of corners.

In some embodiments, the wearable electronic device includes a removable band strap attached to the housing. The set of curved corner protrusions may be configured to cover at least a portion of the removable band strap and retain the removable band strap within a feature formed in the housing. In some cases, the removable band strap is received within a channel of the housing. A portion of the protective case may be configured to peel away from the respective corner of the housing to allow the removable band strap to be removed from the channel of the housing.

Some example embodiments are directed to a wearable electronic device having an enclosure including a housing and a cover defining four corners. The device may also include a band attached to the enclosure and configured to secure the wearable electronic device to a user. A removable case may be attached to the enclosure and include a body disposed over a bottom portion of the housing, multiple protrusions that extend from the body toward the cover to enclose the four corners of the enclosure, and a gasket positioned along a perimeter of an aperture defined in the body and configured to contact a skin of the user to form an optical barrier.

In some embodiments, an optical element is positioned in an opening of the bottom portion of the housing. The optical element may also be positioned within the aperture of the body of the removable case. In some cases, the gasket includes a protrusion that defines a cavity between the skin of the user and the optical element. The cavity formed by the protrusion of the gasket may be substantially free of external light when the wearable electronic device is attached to the user.

In some cases, the at least one protrusion of the multiple protrusions defines a notched portion that is configured to provide access for insertion and removal of the band from the housing. In some cases, the notched portion exposes a receiving channel in the housing for receiving a portion of the band.

Some example embodiments are directed to a protective case configured to attach to a wearable electronic device. The protective case may include a base configured to cover at least a portion of a housing. The case may also include set of protrusions extending from the base and configured to cover at least a portion of a side of the housing. The protective case may also include an annular protrusion extending from the base on a side opposite to the set of protrusions and surrounding an aperture defined within the base. In some cases, the annular protrusion is configured to contact a skin of a wearer when the wearable electronic device is attached to the wearer. The annular protrusion may be formed from a compliant material configured to conform to the skin of the wearer to form an optical seal.

Some embodiments may also include a set of footing protrusions extending from the side of the base, each footing protrusion positioned at a respective corner of the base. The set of footing protrusions may be configured to contact the skin of the wearer when the wearable electronic device is attached to the wearer. In some cases, a membrane structure may be disposed between the set of footing protrusions and the annular protrusion, wherein the membrane structure is configured to conform to the skin of the wearer.

Some embodiments also include a strap retaining portion extending between two protrusions of the set of protrusion, The strap retaining portion may be configured to retain a band within a receiving channel in the housing. In some embodiments, tthe strap retaining portion is configured to peel back to expose an end of the receiving channel for insertion and removal of the band.

In some embodiments, a wearable electronic device may include a housing comprised of a top portion and a bottom portion defining an opening. A band may be attached to the housing and may be configured to secure the wearable electronic device to a user. A case may be formed at least partially over a portion of the housing, and may comprise a body that is substantially disposed on the bottom portion of the housing. A plurality of curved protrusions of the protective case may extend from the bottom portion to the top portion at one or more corners of the housing, and may at least partially cover the top portion at the one or more corners. An aperture may be formed in the body and may correspond to the opening. A gasket may be positioned along a perimeter of the aperture and may be configured to provide a barrier between the aperture and the skin of the user.

BRIEF DESCRIPTION OF THE DRAWINGS

Reference will now be made to representative embodiments illustrated in the accompanying figures. It should be understood that the following descriptions are not intended to limit the disclosure to one preferred embodiment. To the contrary, each is intended to cover alternatives, modifications, and equivalents as may be included within the spirit and scope of the described embodiments as defined by the appended claims.

DETAILED DESCRIPTION

Reference will now be made in detail to representative embodiments illustrated in the accompanying drawings. It should be understood that the following descriptions are not intended to limit the embodiments to one preferred embodiment. To the contrary, it is intended to cover alternatives, modifications, and equivalents as can be included within the spirit and scope of the described embodiments as defined by the appended claims.

The following disclosure relates to a protective case for a wearable electronic device. In particular, the protective case may include features for covering and protecting portions of a housing. The protective case may include elements or portions that are configured to protect external features the wearable electronic device including, for example, the corners and sides of the housing. The protective case may be formed of a compliant material, such as an elastomer, having sufficient rigidity for protecting the wearable electronic device and being sufficiently flexible for attachment to and/or removal from the wearable electronic device. In some instances, the protective case is configured to provide protection from a shock or impact while also allowing the device to operate as well as or better than without the protective case installed.

In some embodiments, the wearable electronic device includes an optical sensor that is configured to interface with the skin of a wearer of the device. In these instances, the protective case may include a gasket having a protrusion that is configured to form a barrier, shield, or optical seal to reduce or prevent external ambient light from affecting measurements performed using the optical sensor. The optical sensor may be specially configured to monitor a physiological and/or health conditions of the user by measuring changes in the optical properties of the user's skin. In some cases, the optical sensor is a photoplethysmogram (PPG) sensor that is configured to measure changes in light absorption properties of the user's skin, which may relate to a In some embodiments, the wearable electronic device is a watch, smartwatch, or other wrist-worn device having detachable straps. In these instances, the protective case may be configured to help retain the detachable straps to the housing. The protective case may also be configured to provide access to attachment features used to secure the straps so that the removable straps may be removed and/or installed while the protective case is in place.

The foregoing and other embodiments are discussed below with reference to FIGS. 1-10. However, those skilled in the art will readily appreciate that the detailed description given herein with respect to these Figures is for explanatory purposes only and should not be construed as limiting.

Figure 1A:
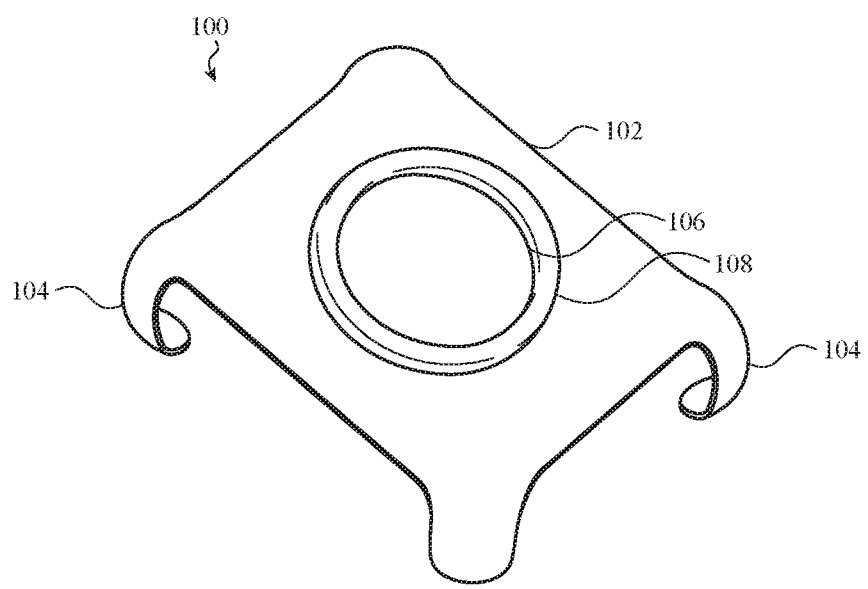
FIG. 1A depicts an example protective case configured to attach to a wearable electronic device.

FIG. 1A depicts an example protective case 100 that is configured to attach to a wearable electronic device. As shown in FIG. 1A, the protective case 100 may be configured to removably engage with a wearable electronic device (e.g., a smart watch) in order to protect the wearable electronic device from impacts or shock. In particular, the protective case 100 includes a set of curved protrusions 104 or bumpers that are configured to protect each respective corner of a set of corners of the wearable electronic device. The curved protrusions 104 extend from a surface of a body portion 102 or base that is configured to cover at least a portion of a rear or lower surface of the wearable electronic device. By providing protection for the corners of the wearable electronic device, the protective case 100 may enhance impact protection without impeding or restricting access to various elements of the wearable electronic device including, for example, buttons, dials, crowns, touch screens, and other similar elements or components.

In some embodiments, the curved protrusions 104 may be formed from a compliant and impact-absorbing material that protects the wearable electronic device. The curved protrusions 104 of the protective case 100 may be configured to conform to and engage respective corners of a wearable electronic device to retain or secure the protective case 100 to the wearable electronic device. In some instances, the curved protrusions 104 are configured to conform to the contoured geometry of the wearable electronic device to form a tight or interference fit. The protective case 100 may be configured to snap onto a housing of a wearable electronic device and be retained without the use of fasteners or adhesive.

The body portion 102 of the protective case 100 may further include an opening or aperture 106 formed in the body portion 102 of the protective case 100. The aperture 106 may be at least partially surrounded by a gasket 108 formed along a perimeter of the opening 106 in the body portion 102. The gasket 108 may include a protrusion or ridge extending from or protruding from a surface of the body portion 102 of the protective case 100. In some cases, the protrusion may contact and form a light barrier, light shield, or other types of seal with a user's skin when the wearable electronic device is attached to a user and the protective case 100 is installed on the wearable electronic device, as further described herein.

In one example, the material forming the protective case 100 is flexible to allow a user to easily attach and/or remove the protective case 100 on a device, while being sufficiently rigid in order to protect the wearable electronic device when the protective case 100 is installed on the wearable electronic device. In some embodiments, the protective case 100 is configured to bend along the body portion 102 and/or the curved protrusions 104 to allow a snap fit or interference fit with a housing of wearable electronic device.

In some embodiments, the protective case 100 may be formed from a compliant material, such as an elastomer. In some cases, the gasket 108 may be integral or integrally formed with the body portion 102 of the protective case 100, and the both the gasket 108 and the body portion 102 may be formed from the same elastomer. In some embodiments, the protective case 100 may be formed using an injection molding process such that the body portion 102 and the gasket 108, integrally formed with the body portion 102, may be from the same material at the same time. Alternatively, the protective case 100 may be formed using a double-shot molding process such that the body portion 102 of the protective case 100 is formed from a first material in a first shot, and the gasket 108, integrally formed with the body portion 102, may be formed from a second material in a second shot. In some embodiments, the gasket 108 is formed as a separate component and is attached to the body portion 102 using an adhesive or fastener.

Figure 1B:
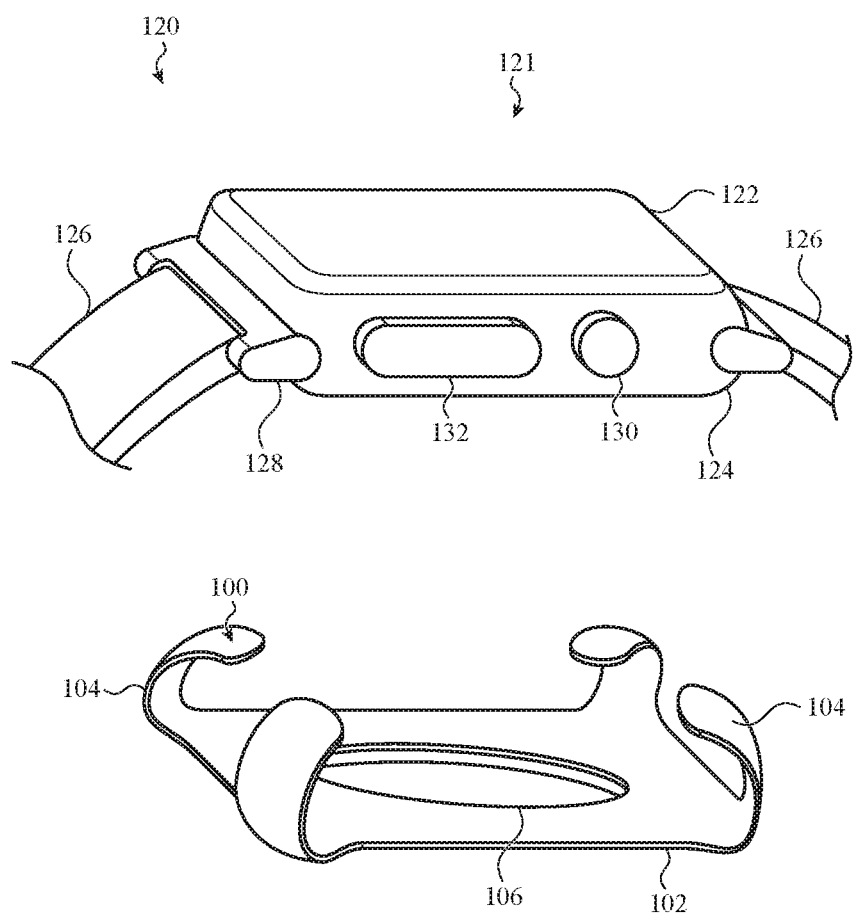
FIG. 1B depicts an exploded view of the example protective case of FIG. 1A and an example wearable electronic device.

FIG. 1B depicts an exploded view of the example protective case 100 of FIG. 1A and an example configuration of a wearable electronic device 120. In particular, FIG. 1B depicts a wearable electronic device 120 that may be configured to be attached to the wrist of a user by a band assembly. This configuration may also be referred to herein as a wearable electronic device, a wearable device, an electronic wristwatch, a smart watch, or simply a device. While these terms may be used with respect to certain embodiments, the functionality provided by the example wearable electronic device 120 may be substantially greater than or vary with respect to many traditional electronic watches or timekeeping devices. Further, although the wearable electronic device 120 is depicted as an electronic wristwatch, it is understood that this is merely an example. In various implementations, the wearable electronic device may be any one of a variety of wearable electronic devices including, for example, a health monitoring device, a tracking device, a time keeping device, a messaging device, and so on. Various embodiments described herein may also be used for other types of portable electronic devices including, for example, a smart phone, mobile phone, tablet computing device, digital media player, mobile computing device, and/or other such portable electronic device that is configured to engagingly mate with a protective case similar to the embodiments described herein.

In the example depicted in FIG. 1B, the wearable electronic device 120 includes a housing 124 and a cover 122. Together, the housing 124 and the cover 122 may define or form an enclosure 121. In general, the enclosure 121 may also surround and provide support to various internal components (including for example integrated circuit chips and other circuitry) which provide computing and functional operations for the wearable electronic device 120. The enclosure 121 may be sealed to provide a substantially water proof or water resistant structure.

The housing 124 and the cover 122 may cooperate to define an external surface or contour shape of the enclosure 121. In the depicted example, the housing 124 is substantially rectangular with round, curved or otherwise contoured corners and side portions. The cover 122 may have a similarly contoured shape that corresponds to the curve or contour of the housing 124. In particular, the cover 122 may have a flat middle portion surrounded by a curved or contoured portion that corresponds to a similarly curved or contoured shape of the housing 124. As shown in FIG. 1B, the geometry of the protective case 100, including the body portion 102 and the curved protrusions 104 or corner elements, may be configured to conform to and/or mate with the corresponding geometry of the enclosure 121, including respective portions of the housing 124 and the cover 122.

The cover 122 may be formed from a transparent material, such as glass or sapphire, to provide protection and visibility for a display positioned within the housing 124. The display may be disposed below the cover 122 and at least partially within a top portion of the housing 124. The cover 122 may also be integrated with a touch and/or force sensor for receiving touch input from a user. In the example of FIG. 1B, the wearable electronic device 120 also includes a button 132 and a crown 130 for accepting input from a user.

As shown in FIG. 1B, the housing 124 of the wearable electronic device 120 may be attached to a user's wrist using a band assembly. The band assembly may include band straps 126 which are attached to the housing 124 via receiving features. In some embodiments, the band straps 126 may include a lug feature 128 that is configured to attach to or be retained by the receiving features (e.g., channels) of the housing 124.

As shown in FIG. 1B, an inner surface of protective case 100 is configured to mate with the flat bottom portion of the housing 124. As discussed in more detail below with respect to FIG. 2B, the aperture 106 formed in the body portion 102 of the protective case 100 is configured to receive or interface with an optical element disposed in an opening formed in the bottom portion of the housing 124. The gasket 108 formed on the outside surface of the body portion 102 of the protective case 100 (as shown in FIG. 1A) may be configured to form a light barrier or light shield between the protective case 100 and the skin of a user to prevent ambient light from entering the optical element when the wearable electronic device 120 is attached to the user.

Figure 2A:
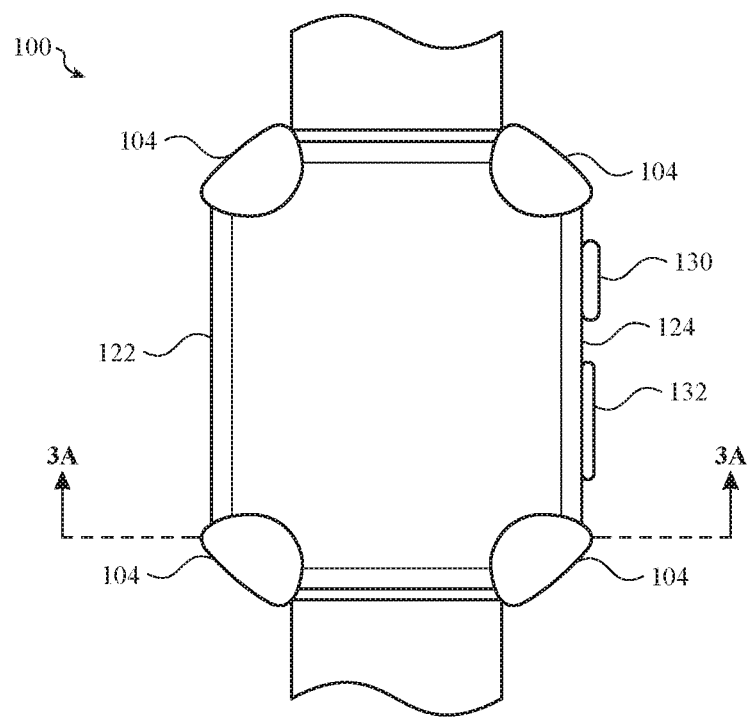
FIG. 2A depicts a top plan view of the wearable electronic device and protective case of FIG. 1B in an assembled configuration.

FIG. 2A depicts a top view of the wearable electronic device 120 and protective case 100 of FIG. 1B in an assembled configuration. As shown in FIG. 2A, the curved protrusions 104 or bumpers of the protective case cover and protect corners of the housing 124 of the wearable electronic device. In some embodiments, wearable electronic device 120 may have a curved side surface that is defined by both the housing 124 and the cover 122. The curved side surface of the housing 124 may have four sides, each side being orthogonal to two adjacent sides and each side being connected to an adjacent side by a rounded corner. The curvature or contour of curved protrusions 104 may correspond to the curvature or contour of the curved side surface of the housing 124. In some embodiments, the curved protrusions 104 may extend from the bottom portion of the housing 124 (as shown in FIG. 2B, below), over the rounded corners of the housing 124, and at least partially over a portion of the cover 122 adjacent to the rounded corner portions of the housing 124.

As shown in FIG. 2A, a portion of the band straps 126 which are attached to the housing 124 may be at least partially covered and retained within a channel or receiving feature of the housing 124 by the curved protrusions 104 of the protective case. Similarly, a portion of the lug feature 128 of the band straps 126 and the receiving features of the housing 124 which receive the lug feature 128 may be at least partially covered and retained within the curved protrusions 104 of the protective case. In this manner, the protective case 100, and specifically the curved protrusion 104 features of the protective case 100 may help to retain and maintain the band straps 126 in a centered position with respect to the housing 124 of the wearable electronic device 120.

Figure 2B:
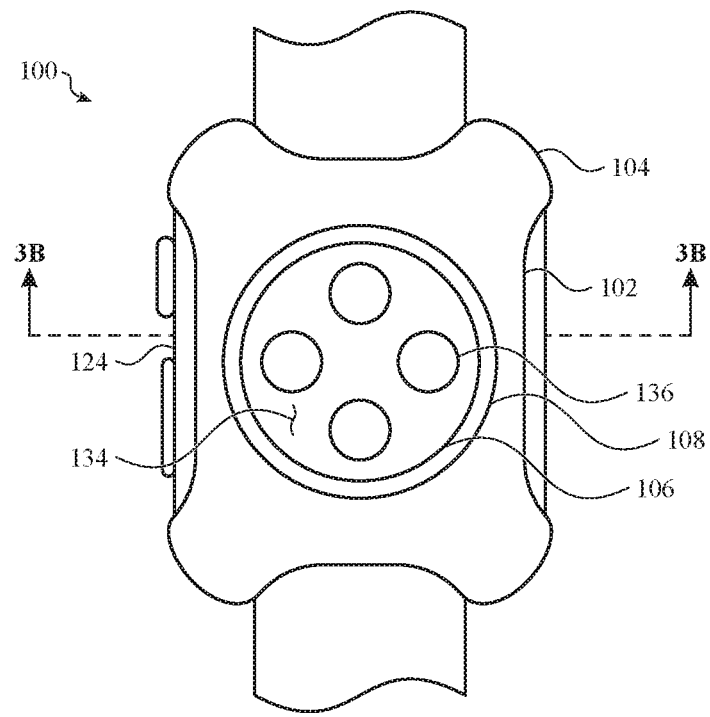
FIG. 2B depicts a bottom plan view of the wearable electronic device and protective case of FIG. 1B in an assembled configuration.
Figure 2C:
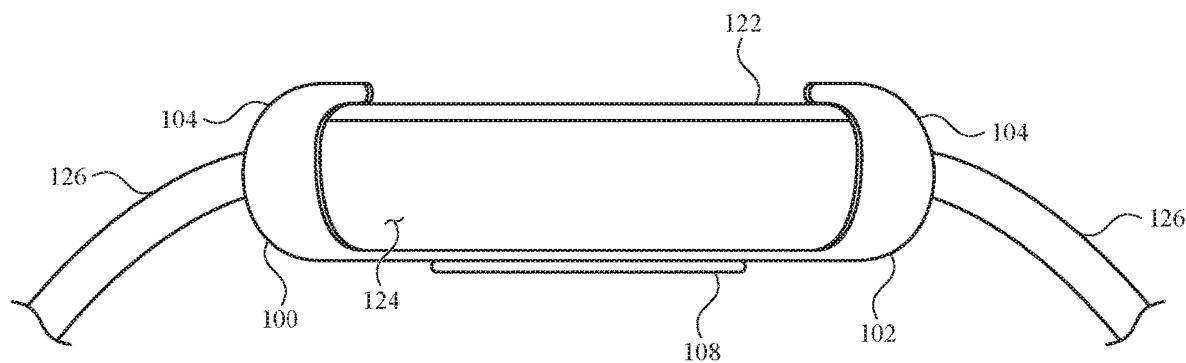
FIGS. 2C and 2D depict side views of the wearable electronic device and protective case of FIG. 1B in assembled configurations.
Figure 2D:
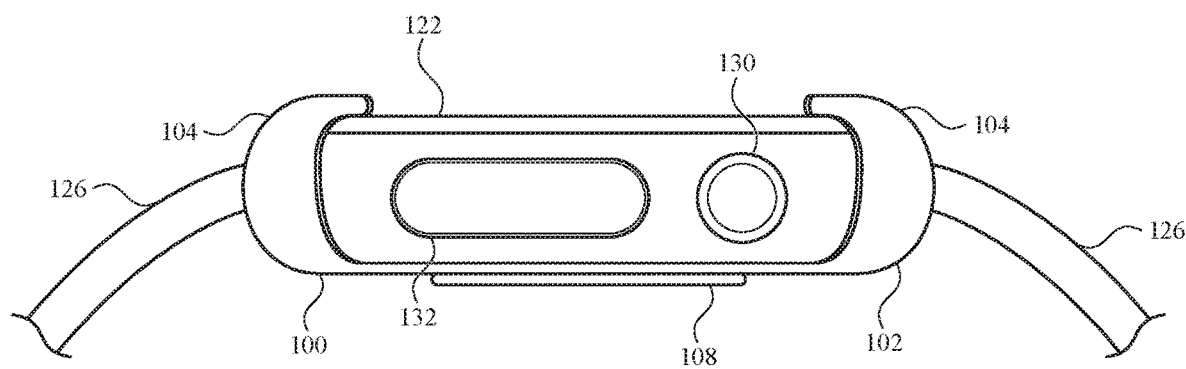

In some embodiments, the curved protrusions 104 of the protective case 100 may partially extend over the cover 122 of the wearable electronic device 120 at the rounded corners of the housing 124, as shown in first and second side views of the protective case 100 attached to the wearable electronic device in FIGS. 2C and 2D. The protective case 100 may at least partially cover or encapsulate the housing 124 and cover 122 of the wearable electronic device. The protective case 100 may be configured to provide impact protection to the wearable electronic device to prevent damage in the event of an accident (e.g., being dropped, bumped, scratched). In some cases, the protective case 100 provides a cushion or a gap between the cover 122 and a potentially damaging surface such as asphalt on the ground if the wearable electronic device is dropped with the cover 122 facing downward. In some embodiments, the protective case 100 may partially extend over the cover 122 so that it does not obstruct the viewable area of the display disposed beneath the cover 122 and it allows access to one or more buttons 132 and a crown 130 disposed within or relative to the housing 124 which are used to receive user input. In some cases, the protective case 100 may partially cover the band straps 126, lug features 128, and receiving features of the housing 124 to allow for the insertion and removal of the band straps 126 from the housing 124 of the wearable electronic device 120.

FIG. 2B depicts a bottom view of the wearable electronic device 120 and protective case 100 of FIG. 1B in an assembled configuration. As shown in FIG. 2B, the protective case 100 may substantially cover the flat bottom portion of the housing 124. In some embodiments, the protective case 100 may include an aperture 106 formed in the body portion 102 of the protective case 100 which is configured to receive an optical element of the wearable electronic device 120. As briefly mentioned above, the wearable electronic device 120 may include an optical element including one or more sensors that can be used to calculate a health metric or other health-related information of the user. In some embodiments, the wearable electronic device may include one or more biosensors (e.g., PPG sensors) or a biosensor module that is disposed in an opening formed in flat bottom portion of the housing 124. In some embodiments, the biosensors are disposed relative to or attached to a rear cover 134 that is formed from an optically transparent material and is configured to be positioned within the opening of the housing 124.

In some cases, the rear cover 134 has an edge that protrudes outwardly from the back surface of the housing 124. In some embodiments, an edge of the rear cover 134 extends past a flat portion of the back surface of the housing 124. The rear cover may also have a convex curved area located between the edges of the rear cover 134. The convex curved area may be formed form an optically transparent material and include one or more windows or apertures that provide operational access to one or more internal components located within the housing 124. For example, the rear cover 134 may provide an optical window for the sensors 136, each sensor 136 may include an optical element or component, such as a light source and/or photodetector. The light sources and/or photodetectors may be configured to detect and measure a physiological condition or property of the user by measuring including, for example, an optical property of the user's skin.

In some embodiments, the convex curved area of the rear cover 134 may protrude at least partially through the aperture 106 of the protective case 100. In some embodiments, the gasket 108 may surround the aperture 106 along a perimeter of the aperture 106 and may form a protrusion which extends away from the body portion 102 of the protective case 100. The convex curved area of the rear cover 134 of the biosensor module may be received within a cavity formed by the protrusion of the gasket 108. In some embodiments, the protrusion of the gasket 108 is an annular protrusion or ridge that is configured to contact a user's skin when the wearable electronic device 120 is attached to the user and forms a barrier or shield for the biosensor module that prevents ambient light from disrupting or affecting the functionality of the light sources and/or photodetectors 136. Aspects of the interaction between the gasket 108 and the optical sensor 136 and rear cover 134 is also discussed below with respect to FIG. 5.

FIGS. 2C and 2D depict side views of the assembled wearable electronic device 120 and protective case 100. As shown in FIGS. 2C and 2D, at the rounded corners of the housing 124, the protective case 100 may cover a bottom portion of the housing 124, may extend from the bottom portion to the curved edge portions of the housing 124, and may extend from the curved edge portions to partially extend over a top surface of the cover 122 of the wearable electronic device 120. As previously discussed, the protective case 100 may partially extend over the cover 122 so that the viewable area of the display disposed beneath the cover 122 is not obstructed by the protective case 100. The protective case 100 may also allow access to the two sides of the housing 124, which includes access to button 132, crown 130, or other similar features disposed thereon that are configured to receive interaction or input from a user.

Figure 3A:
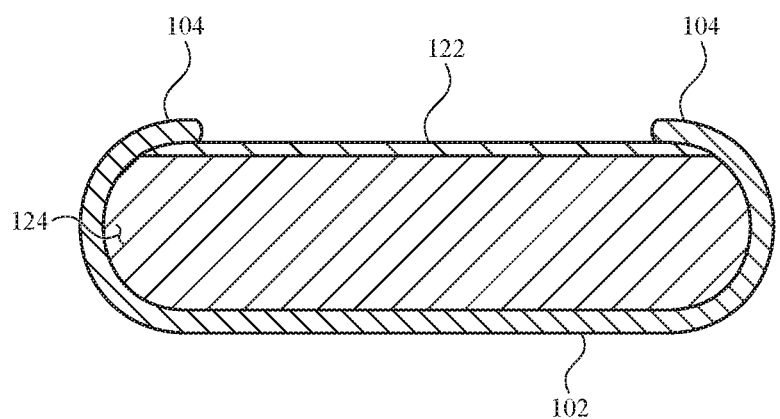
FIG. 3A depicts a cross-sectional view of the assembled wearable electronic device and protective case of FIG. 2A, taken along section A-A.
Figure 3B:
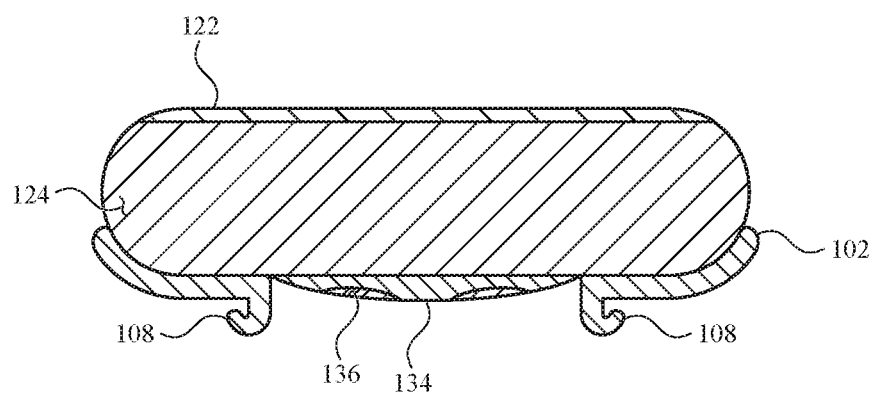
FIG. 3B depicts a cross-sectional view of the assembled wearable electronic device and protective case of FIG. 2B, taken along section B-B.

FIGS. 3A and 3B depict cross-sectional views of the assembled wearable electronic device 120 and protective case 100 of FIGS. 2A and 2B, respectively. As shown in FIG. 3B, the protective case 100 includes an aperture 106 surrounded at its perimeter by a gasket 108. The gasket 108 includes a protrusion (e.g., an annular protrusion or annular rib) which extends away from the body portion or base of the protective case 100. The aperture 106 may receive the convex curved area of the rear cover 134 which may protrude from the housing 124 and into a cavity formed by the protrusion of the gasket 108. The rear cover 134 of the biosensor module may form one or more windows for an optical sensor (e.g., sensor 136 of FIG. 2B) associated the biosensor module. The protective case 100, and specifically the gasket 108 of the protective case, may be configured to form an optical barrier, optical shield or other type of seal with a user's skin in order to reduce stray or external light from reaching the biosensor module (e.g., rear cover 134 and sensors 136) when the wearable electronic device is being worn by a user.

Figure 4:
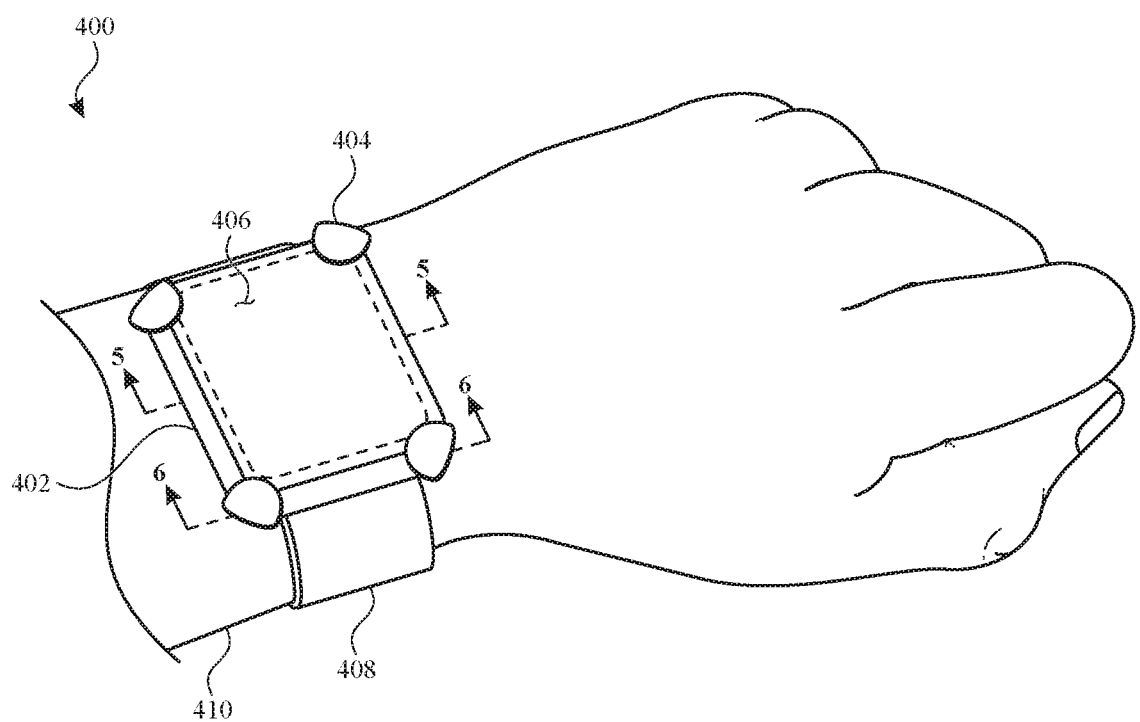
FIG. 4 depicts a wearable electronic device having a protective and secured to the wrist of a user.

FIG. 4 depicts the wearable electronic device attached to a user's wrist 410 while the protective case 400 is installed on the wearable electronic device. In some embodiments, the protective case 400 may provide a barrier between the wearable electronic device and a user's skin along the bottom portion of the housing 402 that would normally directly contact the skin of a user's wrist 410 when the wearable electronic device is being worn by a user. As depicted in FIG. 4, when the wearable electronic device having a protective case 400 installed on a housing 402 of the wearable electronic device is worn by a user, the portions of the protective case 400 covering the corners of the housing 402 are visible to the user. In particular, corner protrusions 404 of the protective case 400 cover the corners of the housing 402 and partially cover a corner portion of a cover 406 disposed over a display of the wearable electronic device. As previously mentioned, the viewable area of the display is substantially unobstructed by the portions of the corner protrusions 404 which extend over a corner portion of the cover 406. In some embodiments, the corner protrusions 404 also help to retain the band 408 on center with the housing 402 and within retaining features for receiving a portion or feature of the band 408 in devices having a removable band feature.

Figure 5:
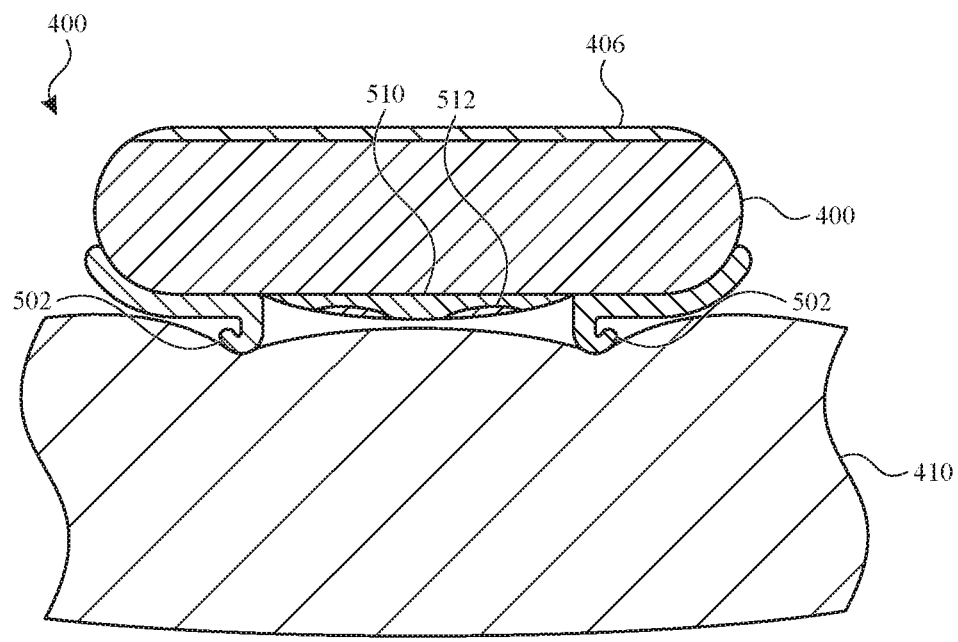
FIG. 5 depicts a cross-section view of the wearable electronic device and protective case of FIG. 4, taken along section C-C, showing the interaction between the protective case and the user's skin.

As shown in greater detail in FIG. 5 in a cross-section view taken along section 5-5 of FIG. 4, a gasket 502 may include a protrusion (e.g., an annular protrusion or annular rib) that extends from a surface of the body portion of the protective case 400. As shown in FIG. 5, the gasket 502 protrudes or extends away from the housing 402 of the wearable electronic device towards the skin of the user's wrist 410 when the wearable electronic device is attached to the user. The protrusion of the gasket 502 may contact the skin of the user's wrist and form a barrier, shield or seal for an optical element or sensor disposed in the housing 402 of the wearable electronic device. In the present example, the gasket 502 surrounds an aperture formed in the bottom portion of the protective case 400, and surrounds an optical element 510 disposed in the housing 402 and received within the aperture. In this manner, the protrusion of the gasket 502 may form a cavity optically coupled to or receiving the optical element 510 having optical sensors 512 disposed therein. The sensors 512 may include optical emitters, optical receivers, and/or other optical components. The optical element 510 may correspond to the biosensor module having sensors 136 described above with respect to FIG. 2B.

In some embodiments, the protrusion of the gasket 502 may contact the user's skin to shield, block, or seal the components of the optical element 510 (e.g., sensors 512) from external or stray light. In some cases, the optical element 510 may be substantially sealed from light on the exterior of the gasket 502, and the light entering and being received by the optical element 510 may be limited to that light emitted by the optical sensors 512 (e.g., optical emitters) of the optical element 510 and reflected by the user's body. Said another way, the optical element 510 may be substantially sealed from ambient light within the cavity formed by the protrusion of the gasket 502 and the user's skin. In some cases, the gasket 502 is configured to conform to the skin of the user to improve the blocking or sealing properties of the gasket 502. While the gasket 502 may form a substantial seal or barrier, the gasket 502 may allow some amount of ambient or external light to reach the optical element 510. In general, the barrier formed by the gasket 502 contacting the user's skin may help to reduce the amount of non-sensor-related light, which may improve the accuracy and reliability of the measurements performed by the optical element 510.

In some embodiments, the material forming the protective case 400 and the gasket 502 may be selected for filtering certain wavelengths of light from the optical element 510. As one example, the wearable electronic device may include an array of light sources and/or detectors that are configured to function as an optical sensor or sensors for measuring and collecting data that may be used to calculate a health metric or other health-related information. In some embodiments, the light sources may operate within a particular light wavelength range. As one example, a light source may include a green LED, which may be adapted for detecting blood perfusion in the body of the wearer. As another example, a light source may include an infrared LED, which may be adapted to detect changes in water content or other properties of the body. An optical sensor having an optical detector may be configured to collect light that is reflected after passing through the user's skin and into the underlying tissue, and to generate a sensor signal based on the reflected light to estimate or compute a health metric or other physiological parameter.

In some embodiments, the gasket 502 may function as a light filter in addition to operating as a barrier to ambient light entering an optical element 510 or biosensor module of the wearable electronic device. In some embodiments, the gasket 502 may be at least substantially opaque to function as a filter for light within a particular wavelength range. For example, the material forming the gasket 502 may function as a filter for light within the wavelength range of that emitted from the green LED, for filtering out other wavelengths of light which may create noise and other adverse effects in the sensor readings.

Figure 6:
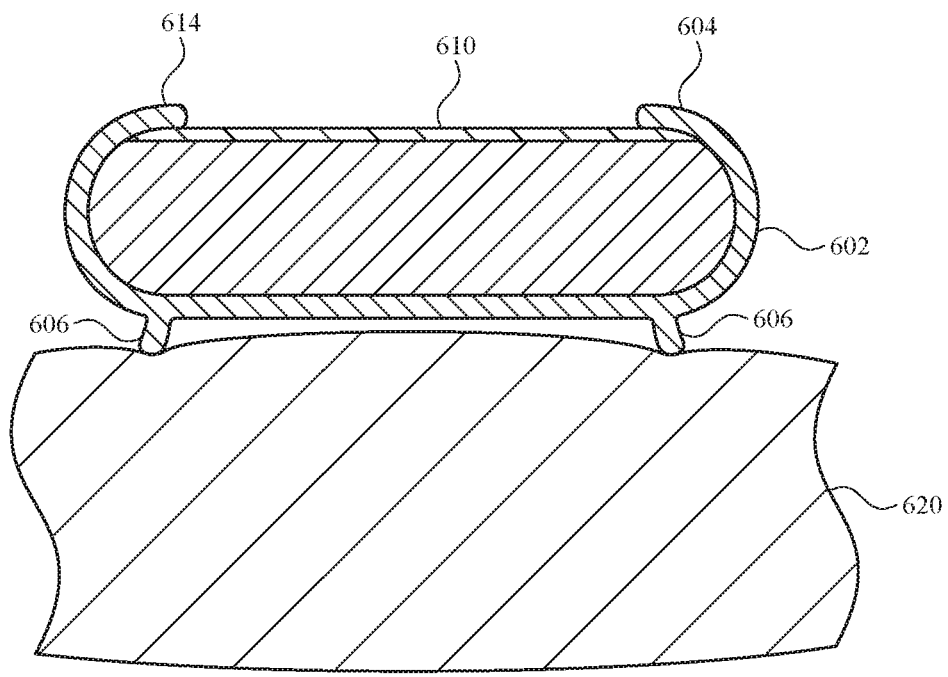
FIG. 6 depicts a cross-section view of the wearable electronic device and protective case of FIG. 4, taken along section D-D, showing protrusions along a bottom surface for interacting with a user's skin.

FIG. 6 depicts an example protective case having a footing protrusion 606 or ridge positioned along a bottom surface of the base or body portion of the protective case. The footing protrusion 606 may be configured to contact the user's skin 620 and help stabilize the wearable electronic device when attached to the wrist of the user. As shown in FIG. 6, the protective case may include a footing protrusion 606 along a bottom perimeter of a device housing 610. In the example, the footing protrusion 606 may be formed in and extend from the body 602 of the protective case and may extend continuously along the bottom perimeter of the housing 610. Alternatively, a plurality of individual protrusions, ridges, or legs may be formed in the protective case along a bottom surface of the housing 610. The footing protrusion 606 may extend from a bottom surface of the protective case and make contact with a user's skin 620. The contact between the user's skin 620 and the footing protrusion 606 may give the wearable electronic device a more stable stance with respect to the wrist of a user. In particular, as the bottom portion of the housing 610 of the wearable electronic device is convex where the optical element 510 is disposed in the housing 610 (not shown in this cross-section), the footing protrusion 606 may help to stabilize or secure the convex surface on the user's wrist 410 by providing a broadened contact surface between the wearable electronic device and the user's wrist 410.

Figure 7:
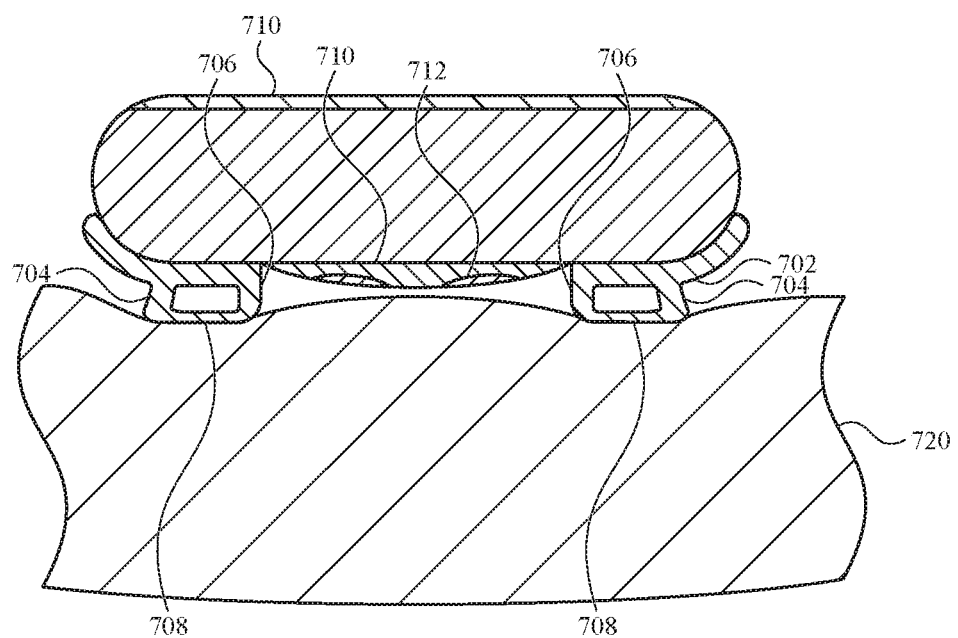
FIG. 7 depicts another example protective case having protrusions along a bottom periphery for providing a light barrier between a user's skin and a sensor element of the wearable electronic device.

FIG. 7 depicts another example embodiment of a protective cover having a footing protrusion. In particular, a protective case may include a footing protrusion 704 that is configured to contact a user's skin 720 to stabilize the device similar to the example described above with respect to FIG. 6. The protective case of FIG. 7 also includes a gasket 706 that is configured to block or shield light similar to as described above with respect to other embodiments. Additionally, the protective case may include a membrane structure 708 or web that extends between the footing protrusion 704 and the gasket 706. The membrane structure 708 may be formed from a soft elastomer or other compliant material. When the wearable electronic device is attached to a user's wrist, the footing protrusion 704 and gasket 706 may contact the user's skin 720 and the membrane structure 708 extending between them may conform with a user's skin 720. In this manner, the membrane structure 708 may form a barrier with the user's skin 720, and may provide improve the light barrier or optical shielding properties of the protective cover.

Figure 8:
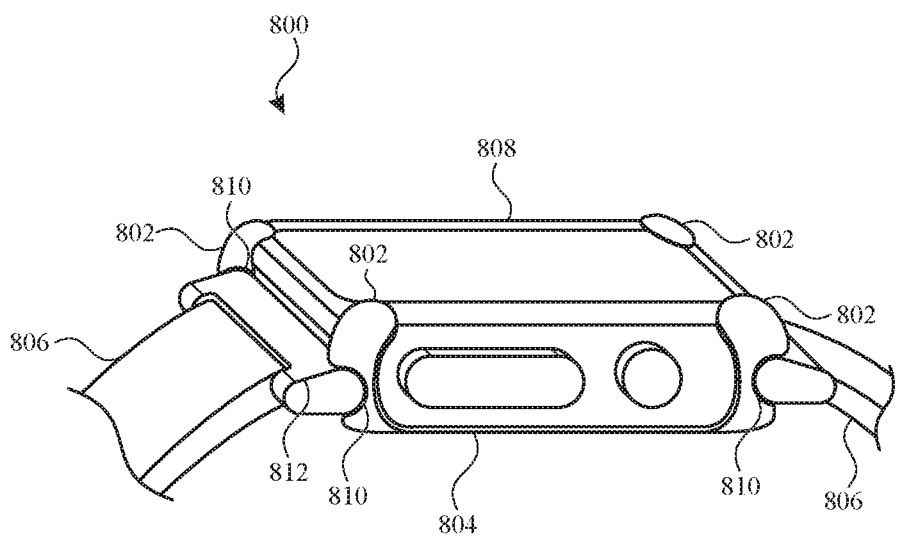
FIG. 8 depicts another example protective case having notched corner elements for insertion and removal of the band of the wearable electronic device.

FIG. 8 depicts another example protective case 800 with curved protrusions 802 or bumpers having notches 810 that provide for the insertion and removal of the band 806 on the wearable electronic device. As shown in FIG. 8, the curved protrusions 802 extending from the body 804 of the protective case 800 may cover rounded corner portions of the housing 808 of a wearable electronic device. As in previous embodiments, the housing 808 may include a channel on one or both ends for receiving a portion of a band 806. In particular, the channel may receive a lug feature 812 formed on an end of the band 806 for insertion and removal of the band 806 on the housing 808 of the wearable electronic device. In some embodiments, the curved protrusions 802 of the protective case 800 may have notches 810 which allow access to the channel on the housing 808 for the lug feature 812 to slide in and out of the channel. In this manner, the notches 810 may allow access to insert and remove the band 806 on the housing 808 of the wearable electronic device.

Figure 9A:
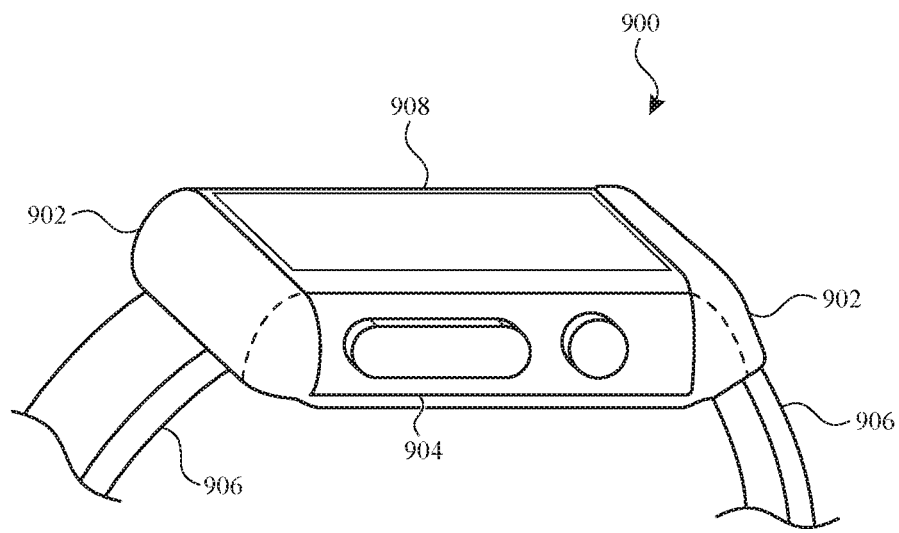
FIG. 9A depicts another example protective case having a surface for retaining a band which is attached to the wearable electronic device.
Figure 9B:
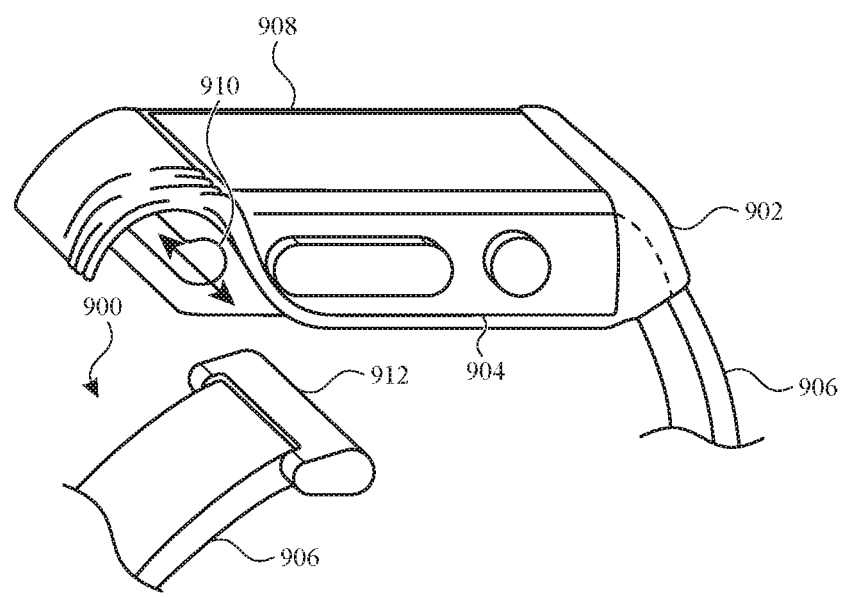
FIG. 9B depicts the protective case of FIG. 9A being peeled back to expose an attachment channel of the wearable electronic device for attaching the band to the wearable electronic device.

In some embodiments, the protective case may have features which not only allow for easy access to attachment elements on the housing of a device for attachment of a band to the wearable electronic device, but also assist in retaining the band on the wearable electronic device when the band or a feature of the band is cooperating with the attachment elements of the housing. As shown in FIGS. 9A and 9B, the protective case 900 may include a strap retaining portion 902 for retaining the band 906 on the housing 904 of the wearable electronic device. The strap retaining portion 902 may help to retain the band 906 in a centered position with respect to the housing 904. In some embodiments, the strap retaining portion 902 also forms the bumper or protective corner similar to the curved corner protrusions described above with respect to the other embodiments. In some cases, the strap retaining portion 902 may be a separate part that extends between or over curved corner protrusions.

As shown in FIGS. 9A and 9B, the strap retaining portion 902 forms a continuous surface which covers a top edge portion of the housing 904 where the band 906 attaches to the housing 904. The strap retaining portion 902 may partially cover a top edge portion of a cover 908 disposed on the housing 904. The strap retaining portion 902 may be configurable to expose a receiving channel 910 formed in the housing 904, so that a lug feature 912 of the band 906 may be inserted and/or removed from the receiving channel 910 in order to attach and/or remove the band 906 from the housing 904. As shown in FIG. 9B, the strap retaining portion 902 may be substantially flexible such that it can be peeled or folded back onto the housing 904 to expose the receiving channel 910. In this manner, the lug feature 912 of the band 906 may be inserted and/or removed from the receiving channel 910. Once the lug feature 912 is received in the receiving channel 910 and the band 906 is ready to be retained on the housing 904, the strap retaining portion 902 may be returned to its initial position to cover and retain the band 906 in position.

Figure 10:
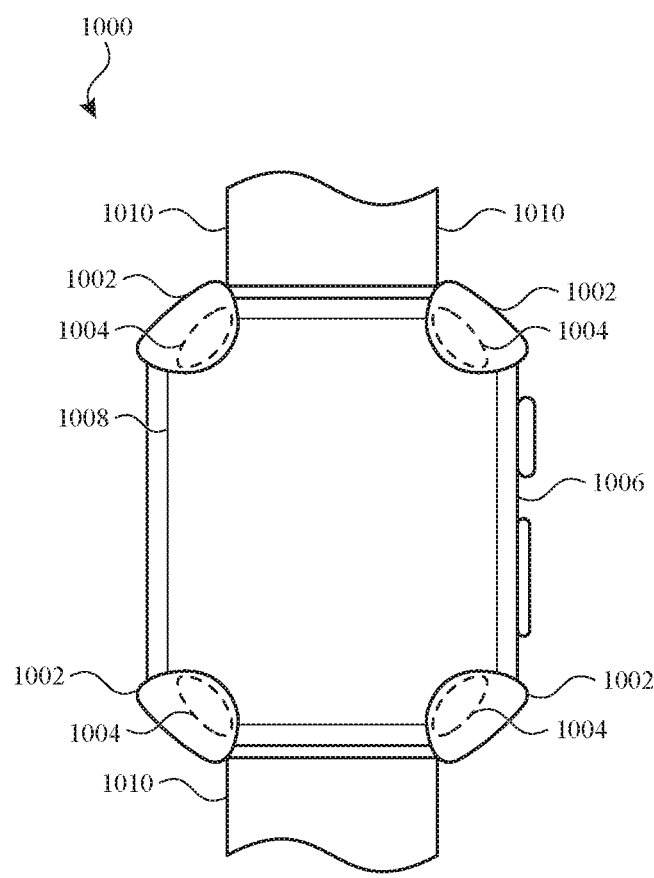
FIG. 10 depicts another example protective case having a rigid element overmolded with a compliant material.

FIG. 10 depicts another example protective case 1000 having a rigid element 1004 disposed at an upper edge of the curved protrusions 1002 of the protective case 1000. In some embodiments, a rigid element 1004 may be overmolded with a compliant material that forms the protective case 1000. As shown in FIG. 10, the rigid element 1004 may be overmolded at an upper edge of the curved protrusions 1002 of the protective case 1000. In this manner, the rigid element 1004 may provide some stability to the curved protrusions 1002 as they are manipulated in order to install the protective case 1000 on the wearable electronic device. In particular, the curved protrusions 1002 formed of a compliant material are bent back in order to "open up" the protective case 1000 to fit it over a housing 1006 of the wearable electronic device, and then are returned to their initial position to install the protective case 1000 on the housing 1006. Additionally, the curved protrusions 1002 are bent back to remove the protective case 1000 from the housing 1006. In this manner, the curved protrusions 1002 experience significant stresses as they are manipulated in order to install and remove the protective case 1000 from the housing 1006 of the wearable electronic device. The rigid element 1004 may add some support to the compliant curved protrusions 1002 as they are flexed back and forth to install and remove the protective case 1000.

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not targeted to be exhaustive or to limit the embodiments to the precise forms disclosed. It will be apparent to one of ordinary skill in the art that many modifications and variations are possible in view of the above teachings.

What is claimed is:

1. A protective case for a wearable electronic device, comprising:
   a body portion configured to at least partially cover a housing of the wearable electronic device and including multiple curved corner protrusions each configured to cover one of multiple corners of the housing, each of the multiple curved corner protrusions extending from a rear surface of the housing to a flat portion of a cover over the housing, the cover being opposite the rear surface and providing a view to a display of the wearable electronic device, wherein each one of adjacent pairs of the curved corner protrusions about the body portion are separated by one of multiple gaps that exposes a portion of the housing, wherein a first one of the adjacent pairs of the curved corner protrusions are arranged to form a first gap for receiving a first band strap extending from the housing and through the first gap, and a second one of the adjacent pairs of the curved corner protrusions are arranged to form a second gap for receiving a second band strap extending from the housing and through the second gap, wherein each of the curved corner protrusions defines a notch that is shaped to provide access for insertion of the band into and removal of the first band strap and the second band strap from the housing while the protective case is attached to the wearable electronic device, wherein each notch is configured to form a shape that matches one or opposing ends of a corresponding channel of the housing; and
   a gasket having a protrusion extending from a surface of the body portion and formed around an aperture defined in the body portion, wherein the protrusion is configured to contact a skin of a wearer when the wearable electronic device is attached to the wearer.

2. The protective case of claim 1, wherein:
   the wearable electronic device includes an optical sensor used to compute a health metric of the wearer;
   the optical sensor is positioned adjacent to the aperture defined in the body portion; ands
   the contact between the protrusion of the gasket and the wearer's skin shields the optical sensor from external light.

3. The protective case of claim 1, wherein:
   each corner of the housing has a contoured shape; and
   each curved corner protrusion of curved corner protrusions is formed from a compliant material and is configured to conform to the contoured shape of the corners.

4. The protective case of claim 1, wherein:
   the wearable electronic device includes a removable band strap attached to the housing; and
   the curved corner protrusions is configured to cover at least a portion of the removable band strap and retain the removable band strap within a feature formed in the housing.

5. The protective case of claim 4, wherein:
   the removable band strap is received within the corresponding channel of the housing; and
   a portion of the protective case is configured to peel away from the respective corner of the housing to allow the removable band strap to be removed from the corresponding channel of the housing.

6. The protective case of claim 1, wherein the gasket is integrally formed with the body portion.

7. The protective case of claim 1, wherein the gasket is formed from a compliant material that is configured to conform to a wrist of the wearer to form an optical seal.

8. A wearable electronic device, comprising:
   an enclosure including a housing, a cover defining four corners and positioned over the housing and a display of the wearable electronic device, and receiving features for coupling the enclosure to band straps of a band assembly;
   a band attached to the enclosure and configured to secure the wearable electronic device to a user; and
   a removable case attached to the enclosure and comprising:
      a body disposed over a bottom portion of the housing, the bottom portion being opposite the cover;
      multiple protrusions that extend from the body to a flat portion of the cover to enclose the four corners of the enclosure and each of the multiple protrusions defining a notched portion that is configured to expose the receiving features and provide access for insertion of the band into and removal of the band from the housing while the removable case is attached to the enclosure, wherein the band, when inserted into one of the receiving features, is configured to extend through a pair of the notched portions of adjacent protrusions; and
      a gasket positioned along a perimeter of an aperture defined in the body and configured to contact a skin of the user to form an optical barrier.

9. The wearable electronic device of claim 8, further comprising:
   an optical element positioned at least partially within the housing, wherein the optical element is substantially aligned with the aperture of the body of the removable case.

10. The wearable electronic device of claim 9, wherein the gasket includes a protrusion that defines a cavity between the skin of the user and the optical element.

11. The wearable electronic device of claim 10, wherein the cavity formed by the protrusion of the gasket is substantially free of external light when the wearable electronic device is attached to the user.

12. The wearable electronic device of claim 8, wherein the notched portion exposes a receiving channel in the housing for receiving a portion of the band.

* * * * *

UNITED STATES PATENT AND TRADEMARK OFFICE
CERTIFICATE OF CORRECTION

PATENT NO. : 10,945,664 B1  
APPLICATION NO. : 15/253846  
DATED : March 16, 2021  
INVENTOR(S) : Michael J. Webb Page 1 of 1

It is certified that error appears in the above-identified patent and that said Letters Patent is hereby corrected as shown below:

In the Claims

Column 13, Line 43 (Claim 2), Replace "ands" with --and--.

Signed and Sealed this  
Twenty-sixth Day of October, 2021

Drew Hirshfeld  
*Performing the Functions and Duties of the*  
*Under Secretary of Commerce for Intellectual Property and*  
*Director of the United States Patent and Trademark Office*